(12) United States Patent
Ferber et al.

(10) Patent No.: US 6,954,961 B2
(45) Date of Patent: Oct. 18, 2005

(54) LIGHT EMITTING TOOTHBRUSH

(75) Inventors: Roman S. Ferber, West Bloomfield, MI (US); John E. Nemazi, Bloomfield Hills, MI (US); Mordechai Lev, West Bloomfield, MI (US)

(73) Assignee: HoMedics, Inc., Commerce Township, MI (US)

( * ) Notice: Subject to any disclaimer, the term of this patent is extended or adjusted under 35 U.S.C. 154(b) by 115 days.

(21) Appl. No.: 10/368,174

(22) Filed: Feb. 18, 2003

(65) Prior Publication Data

US 2003/0205492 A1 Nov. 6, 2003

Related U.S. Application Data

(60) Provisional application No. 60/377,698, filed on May 3, 2002.

(51) Int. Cl.⁷ .............................................. A61C 17/22
(52) U.S. Cl. ........................... 15/22.1; 15/28; 15/167.1; 15/105
(58) Field of Search .......................... 15/105, 22.1, 23, 15/24, 167.1, 28; 433/216

(56) References Cited

U.S. PATENT DOCUMENTS

| | | | |
|---|---|---|---|
| 3,551,932 A | | 1/1971 | Grossman |
| 3,822,432 A | | 7/1974 | Skinner |
| 3,859,684 A | | 1/1975 | Moskwinski |
| 3,939,599 A | | 2/1976 | Henry et al. |
| 4,450,599 A | * | 5/1984 | Scheller et al. ............... 15/22.1 |
| 4,476,604 A | | 10/1984 | White et al. |
| 4,680,825 A | | 7/1987 | White et al. |
| 4,788,734 A | | 12/1988 | Bauer |
| 5,282,291 A | | 2/1994 | Spieler et al. |
| 5,572,762 A | * | 11/1996 | Scheiner ....................... 15/105 |
| 5,673,451 A | | 10/1997 | Moore et al. |
| 5,784,742 A | * | 7/1998 | Giuliani et al. ............... 15/22.1 |
| 5,815,872 A | * | 10/1998 | Meginniss et al. ........... 15/22.1 |
| 6,029,303 A | | 2/2000 | Dewan |
| 6,029,304 A | | 2/2000 | Hulke et al. |
| 6,106,294 A | | 8/2000 | Daniel |
| 6,202,242 B1 | | 3/2001 | Salmon et al. |
| 6,241,362 B1 | | 6/2001 | Morrison |
| 6,327,734 B1 | | 12/2001 | Meginniss, III et al. |
| 6,397,424 B1 | | 6/2002 | Leung |
| 6,536,068 B1 | * | 3/2003 | Yang et al. .................... 15/105 |
| 2003/0135940 A1 | * | 7/2003 | Lev et al. ..................... 15/22.1 |

* cited by examiner

*Primary Examiner*—John Kim
*Assistant Examiner*—Shay L Balsis
(74) *Attorney, Agent, or Firm*—Brooks Kushman P.C.

(57) ABSTRACT

A light emitting toothbrush is provided that includes three light emitting diodes, each having a different primary color. A battery is provided as a power source, and a control circuit is used to control the diodes. The control circuit is configured to sequentially or simultaneously power some or all of the diodes, and it can be configured to vary the power to each diode, thereby providing an almost infinite spectrum of colors of light. A switch is actuated when the brush head contacts an operator's teeth, thereby activating the diodes. A package is provided that allows a potential purchaser to apply a force to the brush head and activate the lights while the toothbrush is still in the package. The control circuit can be configured to control the diodes to provide signals to the operator and/or provide aesthetically pleasing light.

37 Claims, 8 Drawing Sheets

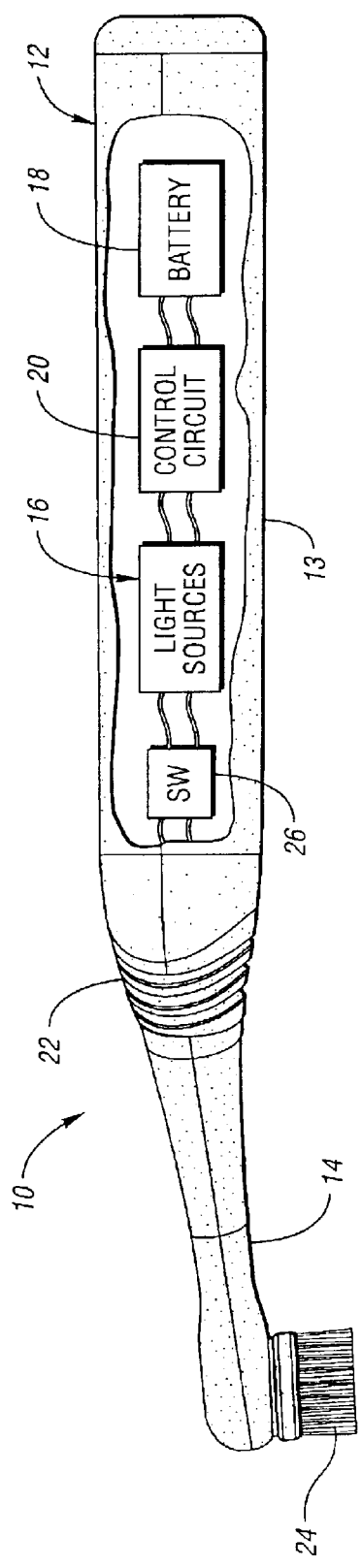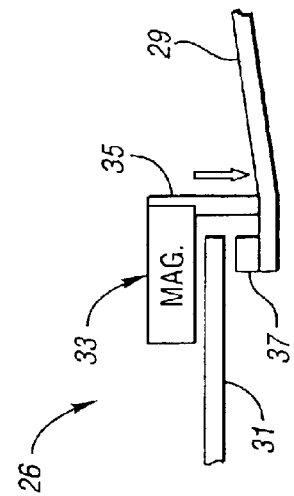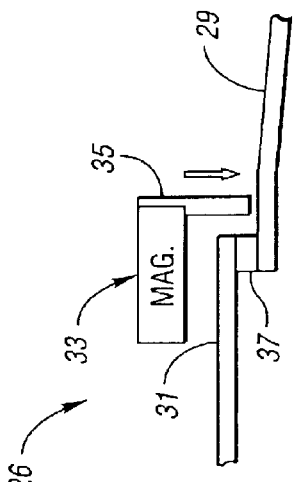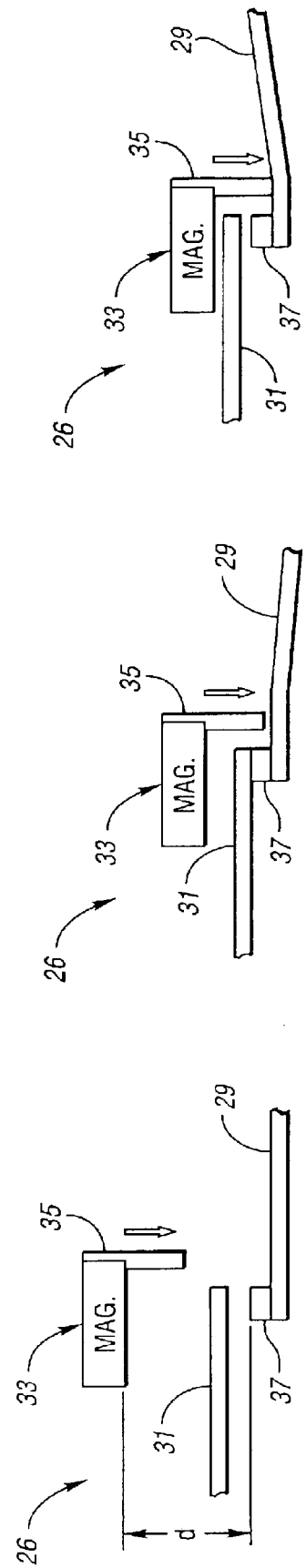

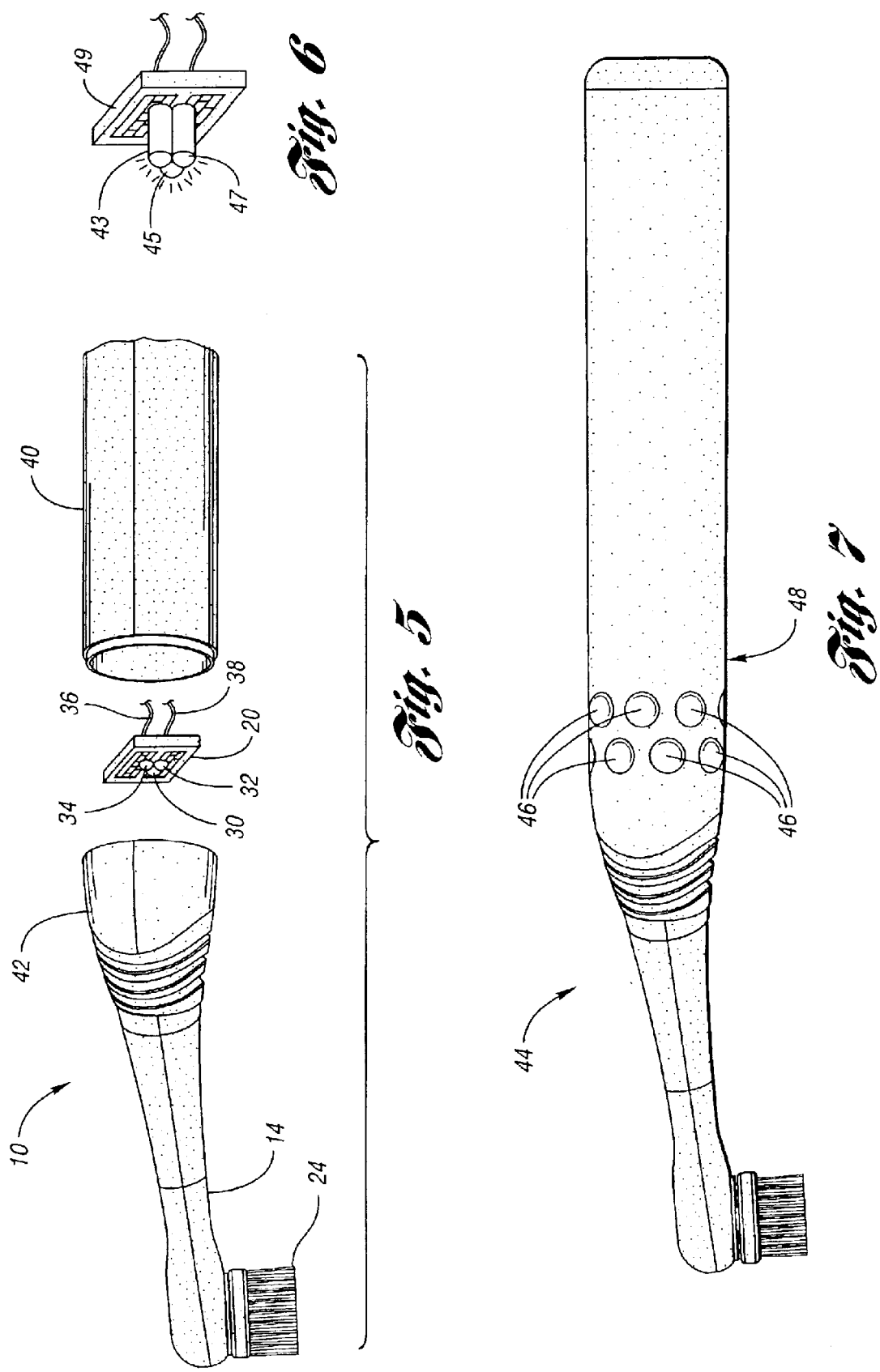

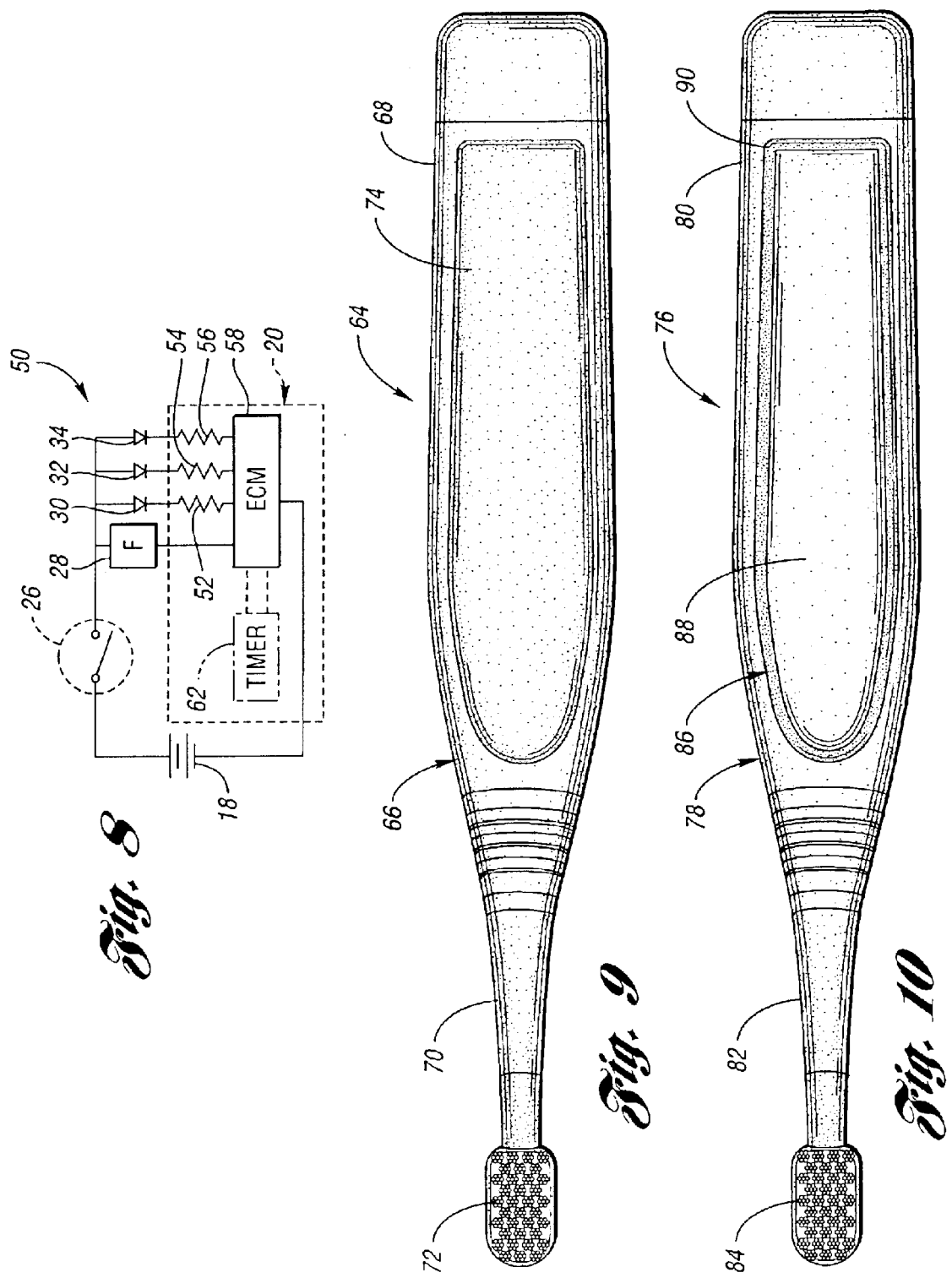

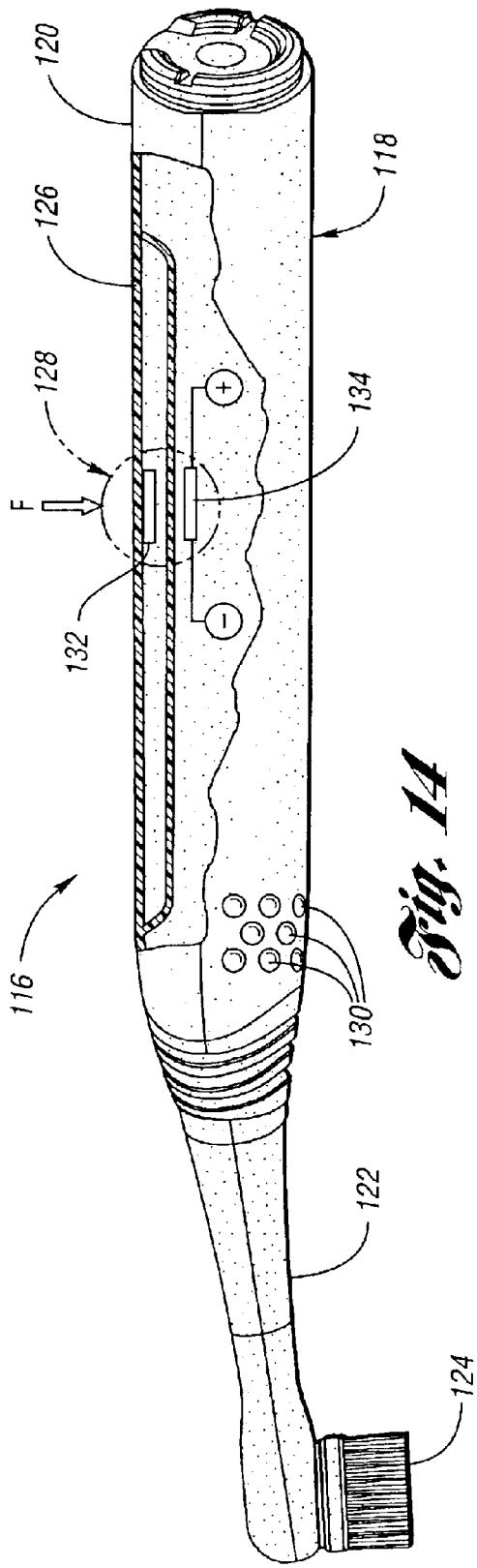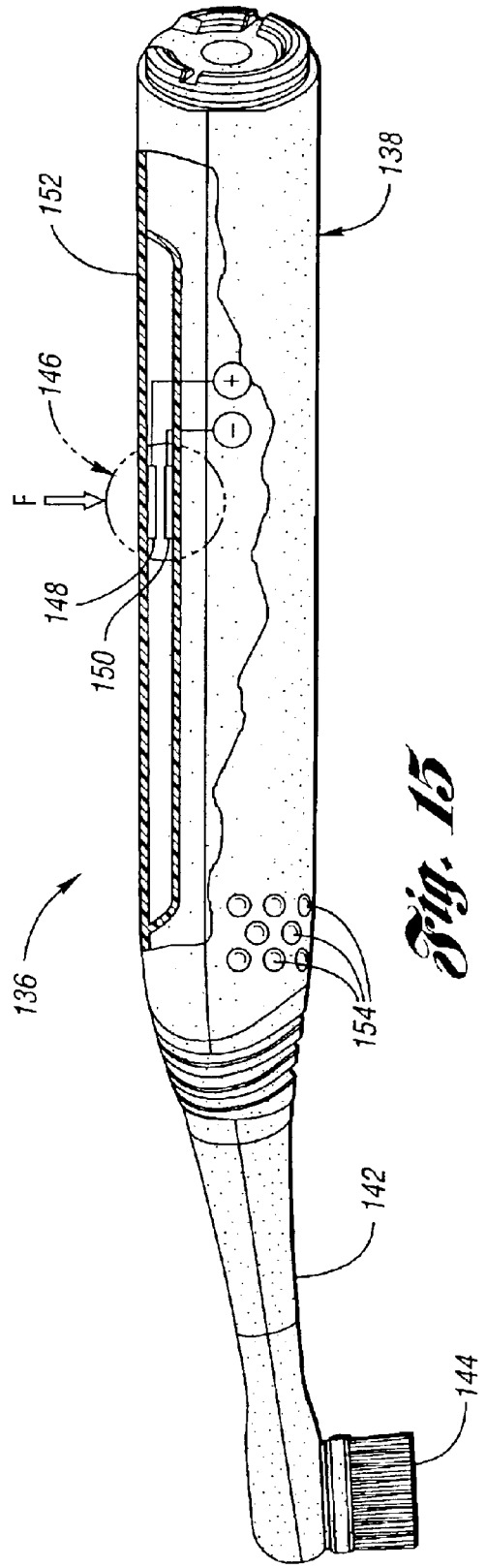

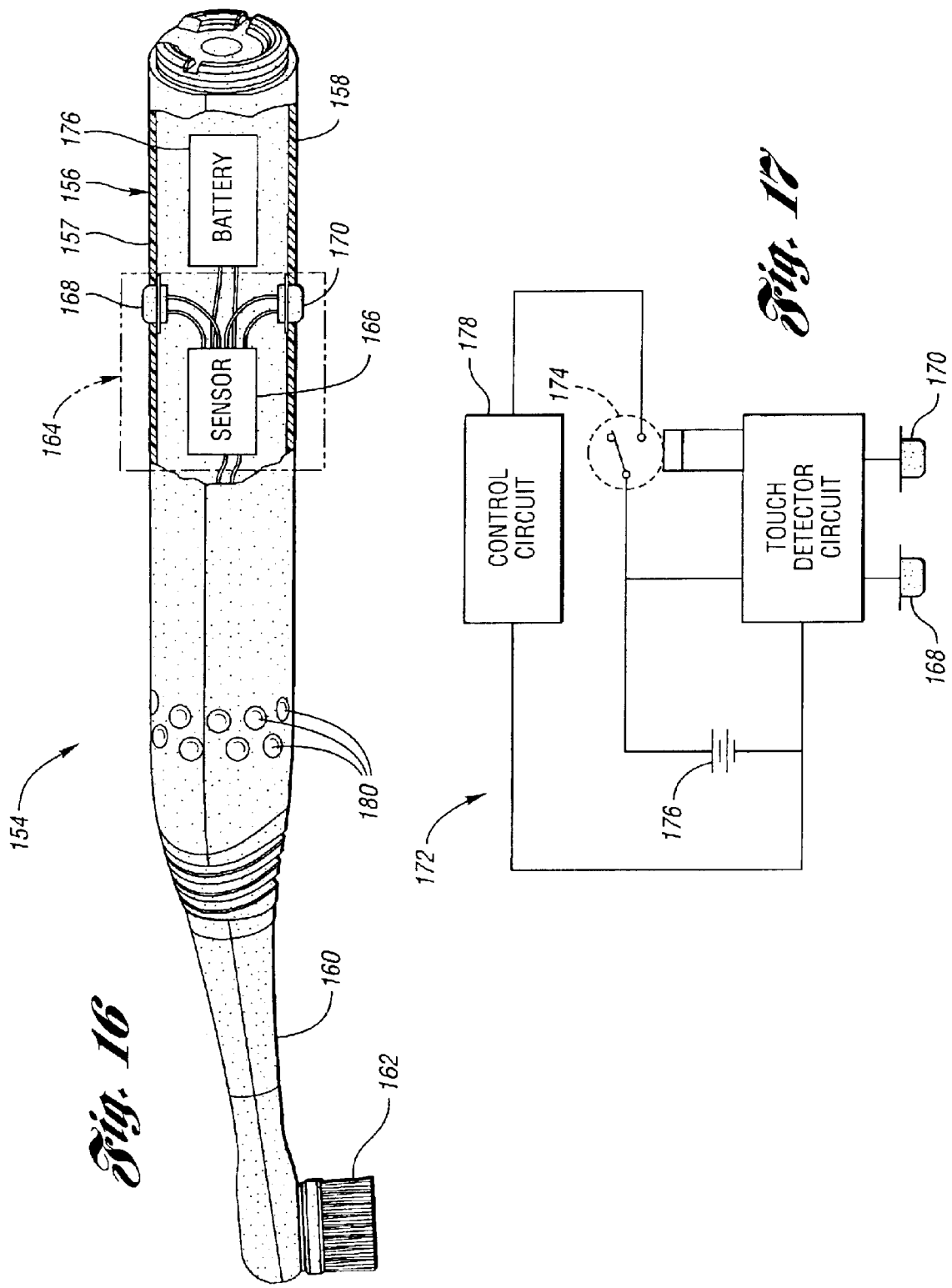

LIGHT EMITTING TOOTHBRUSH

CROSS-REFERENCE TO RELATED APPLICATIONS

This application claims the benefit of U.S. provisional application Ser. No. 60/377,698 filed May 3, 2002, entitled Light Emitting Toothbrush.

BACKGROUND OF THE INVENTION

1. Field of the Invention

The present invention relates to a light emitting toothbrush.

2. Background Art

It has long been known that regular tooth brushing is an effective way to help prevent tooth decay and gum disease. Today, there is a myriad of manual and motorized toothbrushes available to the consumer. Some toothbrushes are designed with specially shaped bristles that claim to provide superior cleaning capabilities, while others have specially shaped handles to more easily facilitate the cleaning of hard-to-reach areas. With regard to motorized toothbrushes, some designs emphasize the speed of the bristle movement, while others focus on the way the bristles move—i.e., rotating, oscillating, reciprocating, or some combination thereof.

Despite the obvious benefits of tooth brushing, improper tooth brushing technique can abrade tooth enamel, especially when an operator applies the toothbrush to the teeth with undo force. This is an issue whether the operator is using a motorized toothbrush or a manual toothbrush. One attempt to overcome this problem is found in U.S. Pat. No. 5,282,291 issued to Spieler et al. on Feb. 1, 1994. Spieler et al. describes a toothbrush handle that includes a warning device that signals an operator when a certain threshold force has been exceeded. The warning signal may be visible, audible, or both. One limitation of Spieler et al. is that the acceptable force level has already been exceeded by the time the warning device alerts the operator. Thus, the operator knows that too much force is being applied only after it is too late.

Accordingly, it is desirable to provide a toothbrush that signals an operator prior to an unacceptably high level of force being exerted on the teeth, and one that also provides pleasing light that may be seen by the operator while using the toothbrush, thus enhancing the brushing experience.

SUMMARY OF THE INVENTION

One aspect of the present invention provides a light emitting toothbrush that visibly signals an operator when a sufficient brushing force is being applied.

Another aspect of the invention provides a light emitting toothbrush that emits light having colors that cover much of the visible spectrum, thereby providing aesthetically pleasing light during use of the toothbrush.

Yet another aspect of the invention provides a light emitting toothbrush that alerts an operator with a light signal when the brush head or toothbrush needs replacing.

Another aspect of the invention provides a light emitting toothbrush having a switch located in a handle portion of the toothbrush such that the switch is actuated and the lights are activated when an operator grips the toothbrush handle.

Still another aspect of the invention provides a light emitting motorizing electric toothbrush having a switch that activates the lights and the toothbrush motor.

Another aspect of the invention provides a light emitting toothbrush in a display package that allows an operator to apply a force to the toothbrush through the package, thereby actuating a switch to active the lights.

Accordingly, a light emitting toothbrush is provided that comprises a toothbrush body that includes a handle portion and a brush head portion. The brush head portion includes a plurality of bristles disposed thereon. A plurality of light sources are disposed adjacent to each other and in relation to the toothbrush body such that at least some of the emitted light is visible from outside the toothbrush body by a user of the toothbrush. The toothbrush also comprises electrical circuitry for controlling the light sources. The electrical circuitry is configurable to automatically vary the intensity of a plurality of the light sources. The toothbrush also includes a switch for activating the light sources.

Another aspect of the invention provides a light emitting toothbrush that comprises a toothbrush body, including a handle portion and a brush head portion. The brush head portion includes a bristle head disposed thereon. The toothbrush further comprises a plurality of light sources disposed adjacent to each other and in relation to the toothbrush body such that at least some of the emitted light is visible from outside the toothbrush body. Electrical circuitry is provided for controlling the lights sources, and is configurable to automatically vary the intensity of a plurality of the light sources. An electric motor is disposed within the toothbrush body for driving the bristle head. A first switch connects the light sources and the motor to an electric source. The first switch has a first position for preventing activation of the light sources and the motor, and a second position for facilitating automatic activation of the light sources and the motor. A second switch has a first position for preventing activation of the light sources and the motor, and a second position for activating the light sources and the motor when the first switch is in the second position.

Yet another aspect of the invention provides a light emitting toothbrush in a display package. The toothbrush and the display package comprise a toothbrush body, including a handle portion and a brush head portion. The brush head portion has a plurality of bristles disposed thereon. A plurality of light sources are disposed adjacent to each other and in relation to the toothbrush body such that at least some of the emitted light is visible from outside the toothbrush body by a user of the toothbrush. Electrical circuitry is provided for controlling the lights sources, and is configurable to automatically vary the intensity of a plurality of the light sources. A switch is provided for connecting the light sources to an electric source. The switch has a first position for preventing activation of the light sources, and a second position for activating the light sources. The switch is placed in the second position when a first predetermined force is applied to the brush head portion. An at least partially translucent package body is configured to at least partially cover the toothbrush. The package body includes a flexible portion disposed proximate the brush head portion. The flexible portion is configured to facilitate application of a force to the brush head portion through the package body to place the switch in the second position.

Another aspect of the invention provides a motorized, light emitting toothbrush in a display package. The toothbrush and display package comprise a toothbrush body, including a handle portion and a brush head portion. The brush head portion has a bristle head disposed thereon. A plurality of light sources are disposed adjacent to each other and in relation to the toothbrush body such that at least some of the emitted light is visible from outside the toothbrush body by a user of the toothbrush. Electrical circuitry is provided for controlling the lights sources, and is configurable to automatically vary the intensity of a plurality of the light sources. An electric motor is disposed within the toothbrush body for driving the bristle head. A first switch connects the light sources and the motor to an electric source. The first switch has a first position for preventing activation of the light sources and the motor, and a second position for facilitating automatic activation of the light sources and the motor. A second switch has a first position for preventing activation of the light sources and the motor, and a second position for activating the light sources and the motor when the first switch is in the second position. The second switch is placed in the second position when a first predetermined force is applied to the brush head portion. An at least partially translucent package body is configured to at least partially cover the toothbrush. The package body includes a flexible portion disposed proximate the brush head portion. The flexible portion is configured to facilitate application of a force to the brush head portion through the package body to place the second switch in the second position.

Still another aspect of the invention provides a light emitting toothbrush in a display package. The toothbrush and the display package comprise a toothbrush body, including a handle portion and a brush head portion. The brush head portion has a plurality of bristles disposed thereon. A plurality of light sources are disposed adjacent to each other and in relation to the toothbrush body such that at least some of the emitted light is visible from outside the toothbrush body by a user of the toothbrush. Electrical circuitry is provided for controlling the lights sources, and is configurable to automatically vary the intensity of a plurality of the light sources. A first switch connects the light sources to an electric source. The first switch has a first position for preventing activation of the light sources, and a second position for facilitating automatic activation of the light sources. A second switch has a first position for preventing activation of the light sources, and a second position for activating the light sources when the first switch is in the second position. An at least partially translucent package body includes a front portion and a back portion configured to cooperate with each other to at least partially cover the toothbrush. The front portion includes a first flexible portion disposed proximate the brush head portion. The first flexible portion is configured to facilitate application of a force to the brush head portion through the package body. The package body includes a second flexible portion disposed proximate the handle portion. The second flexible portion is configured to facilitate application of a force to the handle portion through the package body.

The above object and other objects, features, and advantages of the present invention are readily apparent from the following detailed description of the best modes for carry out the invention when taken in connection with the accompanying drawings.

BRIEF DESCRIPTION OF THE DRAWINGS

FIG. 1 is a simplified descriptive view of a light emitting toothbrush in accordance with a first embodiment of the present invention;

FIG. 2 is a partial fragmentary view of a switch used in the toothbrush shown in FIG. 1, the switch being shown in a first position;

FIG. 3 is a partial fragmentary view of the switch shown in FIG. 2, the switch being shown in a second position;

FIG. 4 is a partial fragmentary view of the switch shown in FIG. 2, the switch being shown in a third position;

FIG. 5 is a partial fragmentary, partially exploded view of the toothbrush shown in FIG. 1;

FIG. 6 is a partial fragmentary perspective view of a light source and a control circuit, the light source comprising three light bulbs;

FIG. 7 is a perspective view of a light emitting toothbrush in accordance with a second embodiment of the present invention;

FIG. 8 is a simplified wiring schematic for the toothbrush shown in FIG. 1;

FIG. 9 is a perspective view of a light emitting toothbrush in accordance with a third embodiment of the present invention, the toothbrush handle portion including a one-piece compressible portion;

FIG. 10 is a perspective view of a light emitting toothbrush in accordance with a fourth embodiment of the present invention, the handle portion including a two-piece compressible portion;

FIG. 14 is a partial fragmentary perspective view of a light emitting toothbrush in accordance with a sixth embodiment of the present invention, the toothbrush having a switch including a Hall effect sensor;

FIG. 15 is a partial fragmentary perspective view of a toothbrush in accordance with a seventh embodiment of the present invention;

FIG. 16 is a partial fragmentary perspective view of a light emitting toothbrush in accordance with an eighth embodiment of the present invention;

FIG. 17 is a simplified wiring schematic illustrating an electrical circuit that can be used with the toothbrush shown in FIG. 16;

DETAILED DESCRIPTION OF THE PREFERRED EMBODIMENTS

Figure 11:
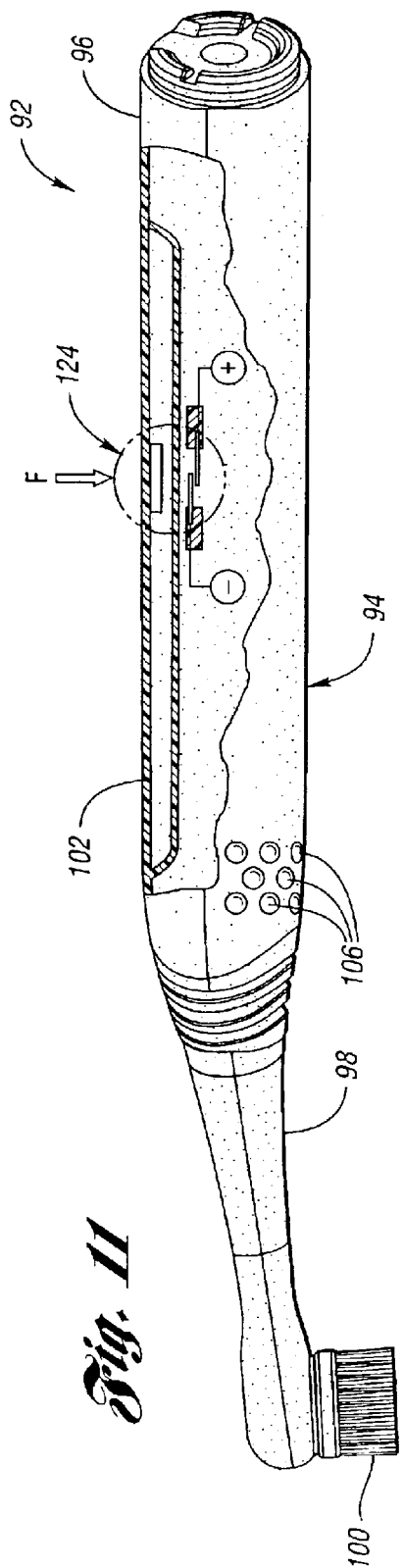
FIG. 11 is partial fragmentary perspective view of a light emitting toothbrush in accordance with a fifth embodiment of the present invention.

FIG. 1 shows a simplified descriptive view of a light emitting toothbrush 10 in accordance with the present invention. The toothbrush 10 includes a toothbrush body 12 that has a handle portion 13 and a brush head portion 14. Disposed in relation to the toothbrush body 12, are light sources 16. Although the light sources 16 are shown in FIG. 1 located within the toothbrush body 12, as explained below, they may also be located outside the toothbrush body. The light sources 16 are powered by a battery 18, and controlled by electrical circuitry, or a control circuit 20. Although only one battery 18 is illustrated in FIG. 1, it is contemplated that more than one battery may also be used. The toothbrush body 12 includes a flexible portion 22 that facilitates some movement of the brush head portion 14 when a force is applied to the brush head portion 14, for example, when bristles 24 are applied to an operator's teeth. A switch 26, which is configured to activate the light sources 16, is actuated when a first predetermined force is applied to the brush head portion 14.

The interaction of the switch 26 and the movement of the brush head portion 14 exemplifies one of the benefits of the present invention. It has been shown that effective brushing occurs when a force of 2N–3N is applied in a direction normal to the teeth. When the brushing force is significantly less than 2N, cleaning of the teeth may not be adequate. When a brushing force of significantly more than 3N is applied to the teeth, unacceptably high levels of enamel abrading may occur. The present invention may be specifically configured to train an operator to use the proper brushing force.

For example, referring to the toothbrush 10 illustrated in FIG. 1, the brush head portion 14 moves slightly as the bristles 24 contact an operator's teeth. As more force is applied, the movement of the brush head portion 14 will increase. It is contemplated that as the force reaches the level of a first predetermined force, for example, a force of approximately 2N, the movement of the brush head portion 14 will actuate the switch 26 and the light sources 16 will be activated. To ensure that the brushing force meets the minimal level desired, the switch 26 may be configured with a spring actuator having an known stiffness. Thus, the switch 26 could be configured such that it is actuated only when a force of at least 2N is applied to the brush head portion 14. Of course, the first predetermined force, or minimum required brushing force, can be changed by configuring the switch 26 with a spring actuator having a different stiffness.

As an alternative to configuring the switch 26 with a spring actuator to control activation of the light sources 16, a load cell, or force sensor 28 (illustrated in FIG. 8 and discussed in more detail below), can be included in the toothbrush 10 to ensure that the light sources 16 are activated upon application of the first predetermined force. By ensuring that the light sources 16 are activated only after this force is applied, an operator will be provided with feedback indicating that enough brushing force is being exerted. Thus, the operator will know that additional application of force is unnecessary. In this way, the operator is alerted when the brushing force is still within an acceptable range, which is a significant improvement over prior art devices which alert an operator only after too much force has been applied.

In addition to providing feedback to an operator to indicate that enough brushing force is being applied, a toothbrush, such as the toothbrush 10, can also be configured to provide feedback to the operator when too much force is being applied. For example, the switch 26 can be configured to stop activation of the light sources 16 when too great a force is applied. FIGS. 2–4 illustrate one possible configuration for the switch 26. As seen in FIG. 2, the switch 26 comprises first and second contact plates 29, 31, and a magnet 33 having a limiting device 35. In FIG. 2, the switch 26 is in a first position, configured to prevent activation of the light sources 16. With no force being applied to the brush head portion 14, the magnet 33 is at a distance (d) from a magnetic contact 37 disposed on the first contact plate 29. The magnetic contact 37 is separated from the second contact plate 31, such that the two contact plates 29, 31 are not electrically connected.

As a force is applied to the brush head portion 14, the magnet 33 begins to move toward the two contact plates 29, 31, until the attraction from the magnet 33 causes the magnetic contact 37 to move toward the magnet 33. The magnetic contact 37 then makes contact with the second contact plate 31, thereby placing the switch 26 in a second position and activating the light sources 16 (see FIG. 3). The switch 26 can be configured so that the magnetic contact 37 is impelled toward the second contact plate 31, only after the first predetermined force has been applied to the brush head portion 14.

FIG. 4 illustrates the switch 26 after too much force has been applied. After the magnetic contact 37 makes contact with the second contact plate 31, application of additional force to the brush head portion will cause the magnet 33 and the limiting device 35 to move even closer to the first contact plate 29. This will continue until the applied force reaches a second predetermined force, at which time the limiting device 35 will separate the two contact plates 29, 31. This places the switch 26 in a third position and stops the activation of the light sources 16 (see FIG. 4.) Thus, by shutting off the light sources 16, an operator is provided with feedback indicating that too much brushing force is being used, and that a reduction in brushing force is recommended. By adjusting various parameters such as the distance between the contact plates 29, 31, the strength of the magnet, and size of the limiting device 35, the first and second predetermined forces can be adjusted. Thus, the switch 26 can be configured to require different amounts of force to activate or stop the light sources 16.

FIG. 5 better illustrates the light sources 16, which comprise three light emitting diodes (LED's) 30, 32, 34, disposed adjacent to each other. The LED's 30, 32, 34 are integrated into the control circuit 20, which has power leads 36, 38 to connect to the battery 18 (shown in FIG. 1). Although three LED's are illustrated in this embodiment, fewer than three or more than three may be used, as desired. One advantage of having three LED's in a light emitting toothbrush, such as the toothbrush 10, is that it makes it possible to provide a wide range of different colored lights. For example, each of the three LED's 30, 32, 34 may be configured to emit a different primary color—e.g., magenta, yellow, cyan. In addition, the control circuit 20 may be configured such that the intensity of each of the LED's 30, 32, 34 can be automatically varied. The variation in intensity, which can be sequential or simultaneous, combined with the disposition of the LED's in close proximity to each other (which allows their respective lights to be blended), means that virtually any color of the visible spectrum may be emitted with just three LED's. The control circuit 20 can also be configured such that the light emitted from the LED's 30, 32, 34 changes color randomly or in predefined patterns. In this way, the light emitted from the toothbrush 10 acts as much more than a mere signaling device, it also significantly enhances the aesthetic pleasure associated with using the toothbrush.

The toothbrush body 12 includes an opaque base portion 40, which houses the battery 18 (shown in FIG. 1), and may house at least a portion of the LED's 30, 32, 34 and the control circuit 20. The toothbrush body 12 also includes a translucent portion 42, which may be clear or shaded as desired. Thus, even when light sources, such as the LED's 30, 32, 34, are located within a toothbrush body, at least some of the emitted light will be visible from outside the toothbrush body by a user of the toothbrush. Although the toothbrush body 12 is illustrated in FIG. 5 as comprising separate opaque and translucent portions 40, 42, a toothbrush body may also be entirely translucent. Moreover, as explained below, a toothbrush body may also be entirely opaque if the light sources are not completely housed within the toothbrush body.

The toothbrush body 12 has a generally cylindrical shape, though it could be made in almost any shape desired. For example, the translucent portion 42 could be beveled or faceted to create a prismatic affect as the emitted light passes through it. As an alternative, a beveled or faceted lens (not shown) can be installed inside the toothbrush body 12 in close proximity to the LED's 30, 32, 34, to diffuse, reflect, and/or refract the emitted light. The minimal space required by the LED's 30, 32, 34 and the control circuit 20, allows for a great deal of design flexibility. Indeed, the present invention contemplates the use of more traditional toothbrush bodies, for example, ones having rectangular cross sections. In addition, the light sources need not be LED's, but rather, may be light bulbs. For example, FIG. 6 shows three light bulbs 43, 45, 47 and a control circuit 49 that can be used with the toothbrush 10 shown in FIGS. 1 and 5. As explained below in conjunction with other embodiments of the invention, light sources are not limited to only one particular kind—e.g., LED's.

As an alternative to locating the light sources within a toothbrush body, light sources may also be at least partially disposed on a toothbrush body. FIG. 7 shows a light emitting toothbrush 44 including a plurality of light sources 46 disposed circumferentially around a toothbrush body 48. Each of the light sources 46 actually includes three separate LED's (not shown individually) located closely adjacent to each other. As described above, such a configuration helps to blend the different colors emitted from the three LED's. Locating the light sources at least partially on the outside of a toothbrush body, such as the toothbrush body 48, eliminates the need to provide a translucent body portion. In addition, the light sources 46 may be configured in virtually any desired pattern. For example, the toothbrush 44, shown in FIG. 7, includes two rows of light sources 46 circumferentially disposed around the toothbrush body 48. Of course, light sources may be aligned in any number of rows, either longitudinally or circumferentially, or alternatively, they need not be aligned in rows at all. Rather, the light sources may be arranged nonlinearly in virtually any desired pattern.

In addition to varying the arrangement of the light sources, the pattern of light generated by any set of light sources may be varied, depending on the configuration of the control circuit. For example, the toothbrush 44 may be configured with a control circuit that allows the individual LED's to be activated simultaneously or sequentially, while at the same time varying the intensity of the light emitted from each of the LED's. This allows each of the light sources 46 to provide virtually any color of light desired. Moreover, the control circuit may be configured to activate the light sources 46 in a sequence that provides a "twinkling" effect. Thus, light sources, such as the light sources 46, may aesthetically enhance the brushing experience, as well as add functionality.

FIG. 8 shows a simple wiring schematic of a circuit 50 that can be used in the embodiment illustrated in FIGS. 1 and 5. The circuit 50 includes the battery 18, the switch 26, the LED's 30, 32, 34, and the control circuit 20. The control circuit 20, includes resisters 52, 54, 56, and an electronic control module (ECM) 58. Any suitable ECM may be used with a control circuit such as the control circuit 20, though a Philips 51 LPC is one type of ECM known to work in this application. As discussed above, activation of the light sources in a light emitting toothbrush, such as the toothbrush 10, may be controlled by a switch that includes a spring having a known stiffness. Alternatively, a load cell, such as the force sensor 28 may be used to sense the force being exerted on the brush head portion 14, and provide a brush force input signal to the ECM 58. This allows the ECM 58 to appropriately control the LED's 30, 32, 34 to provide feedback to an operator based on the brush force input signal. It is readily understood by those skilled in the art that the circuit 50 shown in FIG. 8, represents but one of many circuits that can be used with the present invention. For example, a separate power supply, along with capacitive and additional resistive elements, can be added to the circuit to provide greater control of the power being delivered to the LED's.

In addition to the elements described above, the circuit 50 may also comprise a timing device, or timer 62 (shown in phantom) capable of maintaining a running total of the time the LED's are activated. By providing a timing device, such as the timing device 62, the ECM 58 can be programmed to alert the operator that it is time to replace the toothbrush. Such an alert might be in the form of a specific color—e.g., high intensity red—or may be indicated by a flashing light or series of flashing lights. Thus, the light emitting feature of the present invention serves yet another purpose: helping to ensure that an operator is always using a toothbrush that will clean the teeth effectively. The timer 62 may include a reset device so that when the toothbrush brush head is replaced, the timing beings again at zero. Similarly, the ECM 58 can be programmed to count the number of times the switch 26 is actuated. In such a configuration, the ECM 58 would activate the LED's to alert the operator to replace the toothbrush when the count reaches a predetermined number.

Another use of the timing device 62 is to alert the operator when a recommended length of brushing time as been reached. This can be a signal at the end of the total brushing time, or a number of signals can be given, thereby breaking up the total time into smaller segments. Specifically, it can be beneficial to have each of the four quadrants of the mouth receive an adequate amount of brushing time. With the present invention, a different signal, such as a different color of light or a different flashing sequence, can be used to signal the operator when enough time has been spent brushing each quadrant. This helps to insure that the entire mouth receives an adequate brushing.

The embodiments described thus far have each included a switch that is actuated by a force applied to a brush head portion of a toothbrush body, such as the brush head portion 14 shown in FIGS. 1 and 5. This configuration may be particularly useful when an object of the toothbrush is to train an operator to apply a proper amount of force during brushing. There are however, other ways in which a switch, such as the switch 26, may be actuated. For example, FIG. 9 shows a toothbrush 64 comprising a toothbrush body 66 that includes a handle portion 68 and a brush head portion 70 including bristles 72. The handle portion 68 includes a compressible portion 74 that is configured to be compressed when an operator uses the toothbrush 64. The compressible portion 74 comprises a non-rigid material, such as a elastomer. Alternatively, FIG. 10 shows a toothbrush 76 comprising a toothbrush body 78 including a handle portion 80 and a brush head portion 82, including bristles 84. The handle portion 80 includes a compressible portion 86 that comprises a rigid portion 88 surrounded by a non-rigid portion 90. This configuration may provide a compressible portion having greater stiffness than the compressible portion 74 shown in FIG. 9. In the embodiments shown in FIGS. 9 and 10, the lights may be placed in locations on the outside of the toothbrush bodies 66, 78, or the compressible portions 74, 86 and/or other parts of the toothbrushes 64, 76 may be made from a translucent material to allow lights disposed within the toothbrush bodies 66, 78 to be seen by operators when the toothbrushes are in use.

Figure 12:
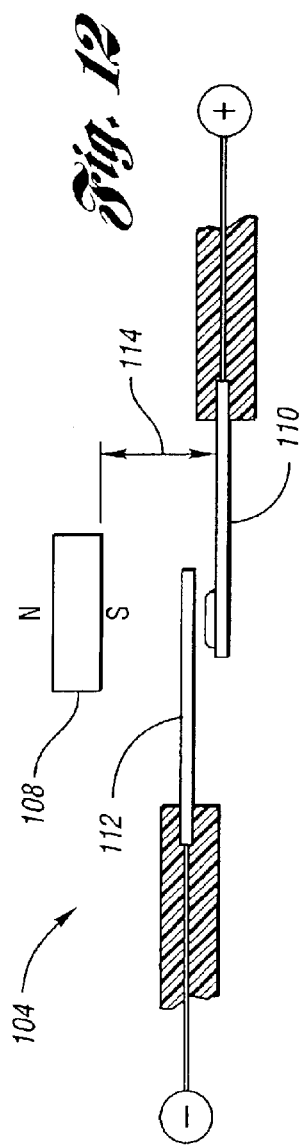
FIG. 12 is a detail view of a switch shown in FIG. 11.
Figure 13:
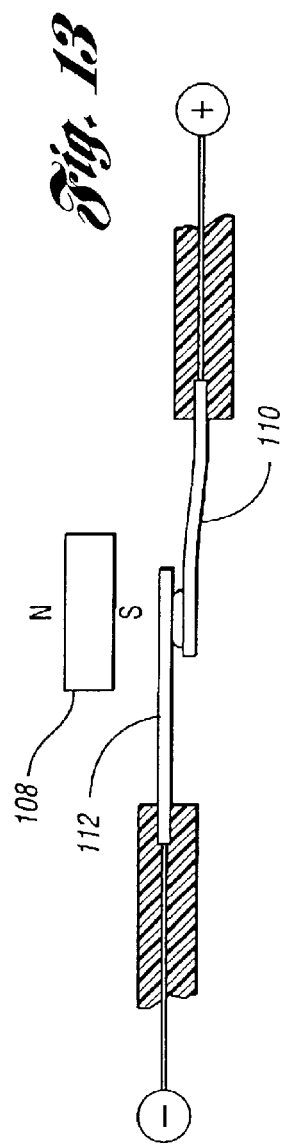
FIG. 13 is a detail view of the switch shown in FIG. 12, the switch being shown in a closed position.

The embodiments shown in FIGS. 9 and 10 have compressible portions 74, 86 disposed on the same side of the toothbrush body as the bristles 72, 84. Of course, a compressible portion of a toothbrush handle portion may be located virtually anywhere on a toothbrush body, for example, on a side of the toothbrush body opposite the bristles. FIG. 11 shows a toothbrush 92 comprising a toothbrush body 94 including a handle portion 96 and a brush head portion 98, having bristles 100. The handle portion 96 includes a compressible portion 102 that is disposed on a side of the toothbrush 92 opposite the bristles 100. A switch 104 is disposed in relation to the compressible portion 102 such that compressing the compressible portion 102 actuates the switch 104. Actuating the switch 104 activates light sources 106 which may be LED's as described above, or may be light bulbs. The switch 104 is shown in detail in FIGS. 12 and 13. The switch 104 includes a magnet 108, a magnetic plate 110, and a nonmagnetic plate 112. When a force (F) is exerted on the compressible portion 102, the force causes the magnet 108 to move in close proximity to the magnetic and nonmagnetic plates 110, 112. When the distance between the magnet 108 and the magnetic plate 110 drops below a fixed distance 114, the two plates 110, 112 contact each other (see FIG. 13), thereby activating the light sources 106.

Other types of switches may be used with a toothbrush having a compressible portion, two of which are shown in FIGS. 14 and 15. FIG. 14 shows a toothbrush 116 comprising a toothbrush body 118 including a handle portion 120 and a brush head portion 122, including bristles 124. The handle portion 118 includes a compressible portion 126. A switch 128 is disposed in relation to the compressible portion 126 such that compressing the compressible portion 126 actuates the switch 128, which activates light sources 130. The switch 128 comprises a magnet 132 and a Hall effect sensor 134. The magnet 132 is located beneath the compressible portion 126 such that application of a force (F) to the compressible portion 126 causes the distance between the magnet 132 and the Hall effect sensor 134 to decrease. When this distance is small enough, current flows through the Hall effect sensor 134 and the light sources 130 are activated.

Another type of switch that can be used in conjunction with a compressible portion on a toothbrush handle is shown in FIG. 15. A toothbrush 136 comprises a toothbrush body 138 including a handle portion 140 and a brush head portion 142, including bristles 144. A switch 146 comprises first and second contact plates 148, 150 disposed in relation to a compressible portion 152 of the handle portion 138 such that compressing the compressible portion 152 causes the two contact plates 148, 150 to move closer to each other until they contact, thereby actuating the switch 146 and activating light sources 154.

FIG. 16 illustrates another way by which light sources in a toothbrush may be activated. A toothbrush 154 comprises a toothbrush body 156 including a handle portion 158 and a brush head portion 160, including bristles 162. The toothbrush 154 includes a sensing device 164 which comprises a capacitive sensor 166 attached to a pair of tactile sensors 168, 170 partially disposed on an external portion 171 of the toothbrush body 156. The presence of an operator's hand on the tactile sensors 168, 170 closes a switch 174 (see FIG. 17) that allows current to flow from a battery 176 to a control circuit 178 for controlling light sources 180. The control circuit 178 may be configured similarly to the control circuit 50 shown in FIG. 8, or may have any configuration suitable to its use in the circuit 172. Thus, the mere presence of an operator's hand on the tactile sensors 168, 170 causes the light sources 180 to emit light according to the programming and configuration of the control circuit 178.

Figure 18:
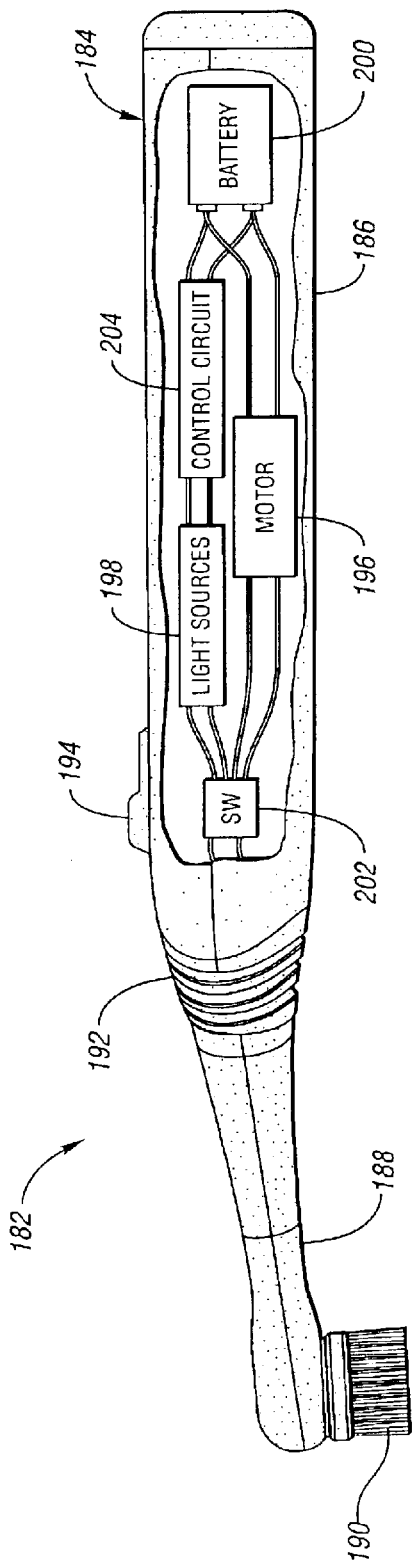
FIG. 18 is a partial fragmentary perspective view of a light emitting toothbrush in accordance with a ninth embodiment of the present invention.

The embodiments thus far described include only manual—i.e., not motorized—toothbrushes. It is important to note that the present invention can be easily utilized with motorized electric toothbrushes as well. FIG. 18 shows a simplified descriptive view of a motorized electric toothbrush 182 in accordance with the present invention. The toothbrush 182 comprises a toothbrush body 184 including a handle portion 186 and a brush head portion 188. The brush head portion 188 includes a bristle head 190. A flexible portion 192 is provided that facilitates some movement of the brush head portion 188 when a force is applied to it. A first switch 194 is disposed on the handle portion 186, and is configured to connect a motor 196 and light sources 198 to an electric source, such as battery 200. When engaged, the motor 196 drives the bristle head 190. The first switch 192 has a first position for preventing activation of the light sources 198 and the motor 196, and a second position for facilitating automatic activation of the light sources 198 and the motor 196.

A second switch 202 is disposed within the toothbrush body 184. The second switch 202 has a first position for preventing activation of the light sources 198 and the motor 196, and a second position for activating the light sources 198 and the motor 196 when the first switch is in the second position. The second switch 202 is placed in the second position when a first predetermined force is applied to the brush head portion 188. As explained more fully below, the force may be applied by a consumer through a display package to evaluate the function of the toothbrush prior to purchase, or it may be applied during use, when the bristle head 190 is brought into contact with an operator's teeth.

As in the previous embodiments, the first predetermined force may be set by using a spring having a known stiffness. Specifically, such a spring may be used to resist a force applied to the brush head portion 188. In this way, the spring force will need to be at least partially overcome—i.e., a force equal to the first predetermined force will need to be applied to the brush head portion 188—in order to place the second switch 202 in the second position. The second switch 202 may also be configured with a third position to stop activation of the light sources 198 and the motor 196 upon application of a second predetermined force. Such a configuration is described in detail above, and illustrated in FIGS. 2–4.

Figure 19:
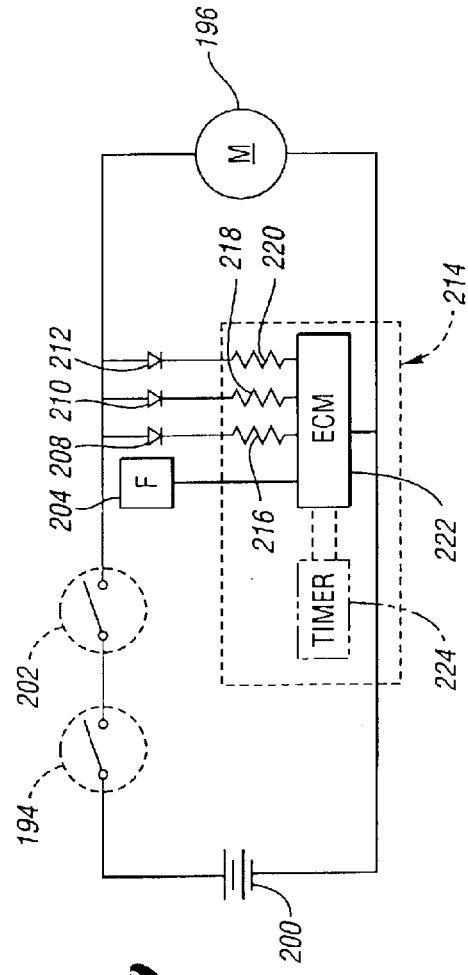
FIG. 19 is a simplified wiring schematic illustrating a circuit that can be used with the toothbrush shown in FIG. 18.

As an alternative to using a spring to control the first predetermined force, a separate load cell, or force sensor 204 may be utilized (see FIG. 19). FIG. 19 shows a simple wiring schematic of a circuit 206 that can be used with a motorized toothbrush 182. As shown in FIG. 19, the light sources 198 comprise three LED's 208, 210, 212, and are controlled by electrical circuitry, or a control circuit 214. Although three LED's 208, 210, 212 are shown in this schematic, fewer than three or more than three may be used, as desired. The LED's 208, 210, 212 may be disposed within the toothbrush body 186 or at least partially on the toothbrush body 186, configured in virtually any pattern desired.

The control circuit 214 includes resisters 216, 218, 220, and an ECM 222. A timing device, or timer 224 (shown in phantom), may be added to the control circuit 214 to maintain a running count of the time the LED's 208, 210, 212 are activated. In this way, the ECM 222 can be programmed to alert the operator that it is time to replace the brush head portion 188, which is removable from the handle portion 186. The ECM 222 can be programmed such that the alert to change the brush head portion 188 comprises a flashing light or series of flashing lights.

The ECM 222 can be programmed to count the number of times the second switch 202 is actuated. This feature can be used as an alternative to the timer 224, or used in conjunction with it. A predetermined number can be programmed into the ECM 222, such that when the count reaches the predetermined number, the ECM 222 activates the LED's 208, 210, 212 to alert the operator that it is time to replace the brush head portion 188. As described above, the timer 224 may also be used to signal the operator that a recommended length of brushing time has been reached.

The force sensor 204 may be used to measure the brushing force and provide a brush force input signal to the control circuit 214, and in particular to the ECM 222. The LED's 208, 210, 212 may then be activated to provide feedback to an operator. The force sensor 204 may also have additional functions. For example, the force sensor 204 may be configured to signal the ECM 222 when the operator is using too much brushing force. The ECM 222 may be configured to open the circuit 206 thereby stopping operation of the motor 200, when excessive brushing force is being used. This illustrates yet another benefit of the present invention: it not only helps to ensure that enough brushing force is being used, but it can be configured to ensure that too much force is not used.

As discussed above, the lights on a light emitting toothbrush may serve a number of purposes. For example, they may be used to alert an operator as to the correct amount of brushing force, they may provide a signal that the brush head needs replacing, or the role of the lights may be aesthetic, helping to provide a more pleasant brushing experience. Of course, the lights may have multiple functions, providing signals to alert an operator and aesthetically enhancing the brushing experience. Regardless of the function of the lights, or their particular configuration, it may be desirable to provide a light emitting toothbrush in a display package for that allows an operator to test the operation of the lights and/or motor prior to purchasing the toothbrush. Specifically, a toothbrush package can be configured to allow a potential purchaser to activate the lights while the toothbrush is still in the package.

Figures 20, 21:
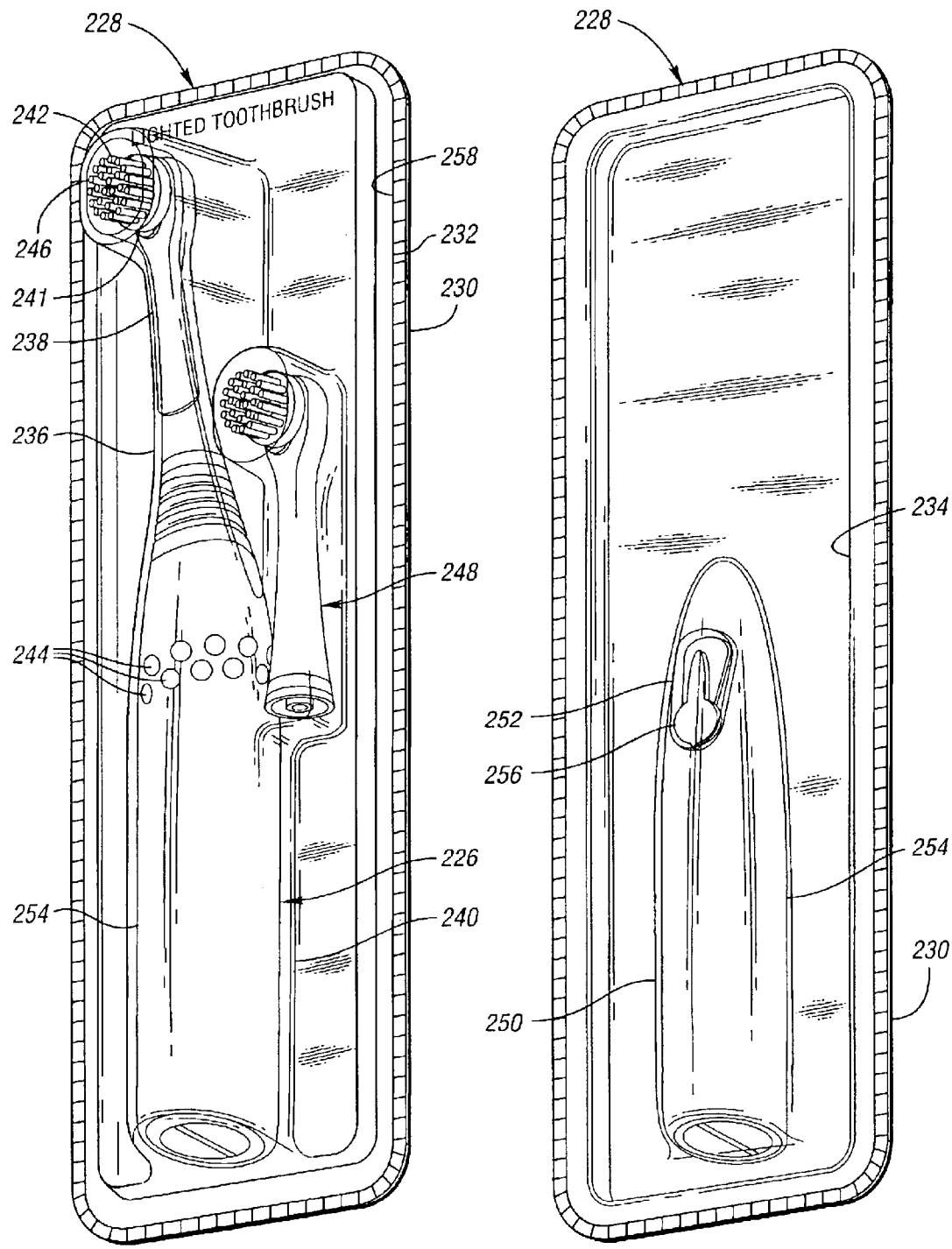
FIG. 20 is a perspective view of a light emitting toothbrush disposed within a package that allows an operator to activate the light sources while the toothbrush is still in the package.
FIG. 21 is a perspective view of the light emitting toothbrush and a back portion of the package shown in FIG. 20.

FIG. 20 shows a light emitting toothbrush 226 inside a display package 228. The package 228 comprises a translucent package body 230 configured to cover the toothbrush 226. The package body includes a front portion 232 and a back portion 234 (shown in FIG. 21). The front portion 232 of the package body 230 includes a first flexible portion 236 disposed proximate a brush head portion 238 of toothbrush body 240. The first flexible portion 236 is configured to allow an operator to apply a force to the brush head portion 238 through the package body 230. This causes movement of the brush head portion 238 in the direction of the force.

Similar to the toothbrush 182 shown in FIG. 18, the toothbrush 226 includes a second switch (not visible) that is placed in a second position when a force is applied to the brush head portion 238. The second switch activates a motor (not visible) that drives a bristle head 241. The bristle head 241 is disposed on the brush head portion 238, and includes a plurality of bristles 242. The second switch also activates light sources 244 disposed circumferentially around the toothbrush body 240. Thus, when an operator applies a force to the brush head portion 238, at the first flexible portion 236, the brush head portion 238 moves in the direction of the applied force, and the second switch is placed in the second position. This allows the operator to observe the lights and the movement of the bristle head 241 while the toothbrush is still in the package 228.

The front portion 232 of the package body 230 also includes a first relatively non-flexible portion 246 disposed proximate the bristle head 241 and the bristles 242. The first relatively non-flexible portion 246 provides protection for the bristles 242, so that they are not damaged when potential purchasers repeatedly press on the brush head portion 238 to actuate the second switch to observe the lights and/or the movement of the bristle head 241. As used here, the term "relatively non-flexible" refers to portions of the package body 230 which are not easily deflected. In general, if enough force is applied to the package body 230 to cause deflection of the relatively non-flexible portions, permanent deformation of the package body may result. Thus, the relatively non-flexible portions are configured such that their deflection is thereby discouraged. The package body 230 is configured to receive not only the toothbrush 226, but also a separate toothbrush brush head portion 248. In this way, the packaging provides yet another advantage to the consumer: the additional brush head portion 248 accommodates two users, or provides a spare brush head for a single user.

FIG. 21 shows the back portion 234 of the package body 230. The back portion 234 includes a second flexible portion 250, and a second relatively non-flexible portion 252. The second flexible portion 250 is disposed proximate a handle portion 254 of the toothbrush body 240. The positioning of the second flexible portion 250 allows an operator to apply a force to the handle portion 24 through the package body 230. Thus, the package 228 accommodates light emitting toothbrushes having a switch actuated by the application of force to the brush head portion, such as the toothbrush 226, as well as those having a switch actuated by compressing a compressible portion of the handle (see FIGS. 11 and 14–15).

The second relatively non-flexible portion 252 is located proximate a first switch 256. Similar to the first switch 194, described above in conjunction with the toothbrush 182 shown in FIG. 18, the first switch 256 is configured to prevent activation of the light sources 244 and the motor, and to facilitate automatic activation of the light sources 244 and the motor. For example, when the first switch 256 is in the second, or "on" position, pressure applied to the brush head portion 238 will activate the motor and the light sources 244. In contrast, when the first switch is in the first, or "off" position, applying a force to the brush head portion 238 will not activate the motor or the light sources 244. Thus, the second relatively non-flexible portion 252 allows a manufacturer to set the first switch into either the "on" or "off" position, with the confidence that the consumer cannot easily change the position through the package.

The package body 230 may be made from a thermoplastic material which is easily molded into different shapes to accommodate many styles of toothbrushes. Of course, the package body may be made from other suitable materials, including other types of polymers. A thermoplastic material can be transparent, or made in an almost infinite variety of colors. It also provides a combination of flexibility and stiffness, depending on the amount of material used, and the geometry into which it is molded. For example, portions of the package body 230 may be made more or less flexible by increasing or decreasing the thickness of material. In addition, the package body may be configured with a stiff portion by providing relatively straight sides with a flat upper portion (see the first relatively non-flexible portion 246), or it may be configured with a flexible portion by providing curved sides that blend into a curved upper portion (see first and second flexible portions 236, 250.) The translucent nature of the thermoplastic material allows for the placement of an information card 258 adjacent the front and back portions 232, 234. The information card 258 may contain logos and the like, as well as instructions as to the proper use of the toothbrush 226.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A light emitting toothbrush, comprising:
   a toothbrush body, including a handle portion and a brush head portion, the brush head portion having a plurality of bristles disposed thereon;
   a plurality of light sources disposed adjacent to each other in relation to the toothbrush body such that at least some of the emitted light is visible from outside the toothbrush body by a user of the toothbrush;
   electrical circuitry for controlling the light sources, the electrical circuitry being configured to automatically vary the intensity of a plurality of the light sources while at least some of the light sources are activated, the automatic variation in intensity being independent from the magnitude of a force applied to the brush head portion; and
   a switch for activating the light sources.

2. The light emitting toothbrush of claim 1, wherein the electrical circuitry can be configured to automatically sequentially vary the intensity of the light emitted from a plurality of the light sources.

3. The light emitting toothbrush of claim 1, wherein the electrical circuitry can be configured to automatically simultaneously vary the intensity of the light emitted from each of the light sources.

4. The light emitting toothbrush of claim 1, wherein the switch is configured to be actuated when a first predetermined force is applied to the brush head portion.

5. The light emitting toothbrush of claim 4, wherein the switch has a first position for preventing activation of the light sources, a second position for activating the light sources, and a third position for stopping activation of the light sources, the switch being placed in the second position when the first predetermined force is applied to the brush head portion, the switch being placed in the third position when a second predetermined force is applied to the brush head portion, the second predetermined force being greater than the first predetermined force.

6. The light emitting toothbrush of claim 1, wherein the handle portion includes a compressible portion, and wherein the switch is disposed in relation to the compressible portion such that compressing the compressible portion actuates the switch.

7. The light emitting toothbrush of claim 6, wherein the switch comprises a magnet, a magnetic plate, and a non-magnetic plate, and wherein compressing the compressible portion moves the magnet in close proximity to the magnetic plate, thereby effecting an electrical connection between the magnetic plate and the non-magnetic plate.

8. The light emitting toothbrush of claim 6, wherein the switch comprises a magnet and a Hall effect sensor, and wherein compressing the compressible portion moves the magnet in close proximity to the Hall effect sensor, thereby effecting a flow of current through the Hall effect sensor.

9. The light emitting toothbrush of claim 6, wherein the switch comprises a pair of contact plates, and wherein compressing the compressible portion causes the contact plates to contact each other, thereby effecting an electrical connection between the contact plates.

10. The light emitting toothbrush of claim 6, wherein the compressible portion comprises a rigid portion and a non-rigid portion.

11. The light emitting toothbrush of claim 6, wherein the compressible portion comprises a non-rigid material.

12. The light emitting toothbrush of claim 1, wherein the switch comprises a sensing device, at least a portion of which is disposed on an exterior portion of the toothbrush body, and wherein the switch is actuated by the presence of the operator's hand on the sensing device.

13. The light emitting toothbrush of claim 12, wherein the sensing device includes a capacitive sensor.

14. The light emitting toothbrush of claim 1, wherein the light sources comprise three light bulbs, each light bulb emitting a different primary color.

15. The light emitting toothbrush of claim 1, wherein the light sources comprise at least three light emitting diodes, with each of the light emitting diodes emitting a different primary color.

16. The light emitting toothbrush of claim 1, wherein at least a portion of the toothbrush body is translucent.

17. The light emitting toothbrush of claim 1, further comprising a load cell capable of measuring the force applied to the brush head portion, and configured to provide a brush force input signal to the electrical circuitry or controlling the light source to provide feedback to an operator.

18. The light emitting toothbrush of claim 1, wherein the electrical circuitry can be configured to count the number of times the switch is actuated.

19. The light emitting toothbrush of claim 1, wherein the electrical circuitry includes a timing device to measure the time the switch is actuated.

20. A light emitting toothbrush, comprising:
   a toothbrush body, including a handle portion and a brush head portion, the brush head portion having a bristle head disposed thereon;
   a plurality of light sources disposed adjacent to each other and in relation to the toothbrush body such that at least some of the emitted light is visible from outside the toothbrush body by a user of the toothbrush;
   electrical circuitry for controlling the light sources, the electrical circuitry being configured to automatically vary the intensity of a plurality of the light sources;
   an electric motor disposed within the toothbrush body for driving the bristle head;
   a first switch for connecting the light sources and the motor to an electric source, the first switch having a first position for preventing activation of the light sources and the motor, and a second position for facilitating automatic activation of the light sources and the motor; and
   a second switch having a first position for preventing activation of the light sources and the motor, and a second position for activating the light sources and the motor when the first switch is in the second position.

21. The light emitting toothbrush of claim 20, wherein the electrical circuitry can be configured to automatically sequentially vary the intensity of the light emitted from a plurality of the light sources.

22. The light emitting toothbrush of claim 20, wherein the electrical circuitry can be configured to automatically simultaneously vary the intensity of the light emitted from each of the light sources.

23. The light emitting toothbrush of claim 20, wherein the second switch is placed in the second position when a first predetermined force is applied to the brush head portion.

24. The light emitting toothbrush of claim 23, wherein the second switch has a third position for stopping activation of the light sources and the motor, the second switch being placed in the third position when a second predetermined force is applied to the brush head portion, the second predetermined force being greater than the first predetermined force.

25. The light emitting toothbrush of claim 20, wherein the handle portion includes a compressible portion, and wherein the second switch is disposed in relation to the compressible portion such that compressing the compressible portion actuates the second switch.

26. The light emitting toothbrush of claim 25, wherein the second switch comprises a magnet, a magnetic plate, and a non-magnetic plate, and wherein compressing the compressible portion moves the magnet in close proximity to the magnetic plate, thereby effecting an electrical connection between the magnetic plate and the non-magnetic plate.

27. The light emitting toothbrush of claim 25, wherein the second switch comprises a magnet and a Hall effect sensor, and wherein compressing the compressible portion moves the magnet in close proximity to the Hall effect sensor, thereby effecting a flow of current through the Hall effect sensor.

28. The light emitting toothbrush of claim 25, wherein the second switch comprises a pair of contact plates, and wherein compressing the compressible portion causes the contact plates to contact each other, thereby effecting an electrical connection between the contact plates.

29. The light emitting toothbrush of claim 25, wherein the compressible portion comprises a rigid portion and a non-rigid portion.

30. The light emitting toothbrush of claim 25, wherein the compressible portion comprises a non-rigid material.

31. The light emitting toothbrush of claim 20, wherein the second switch comprises a sensing device, at least a portion of which is disposed on an exterior portion of the toothbrush body, and wherein the switch is actuated by the presence of the operator's hand on the sensing device.

32. The light emitting toothbrush of claim 20, wherein the light sources comprise three light bulbs, each light bulb emitting a different primary color.

33. The light emitting toothbrush of claim 20, wherein the light sources comprise at least three light emitting diodes, with each diode emitting a different primary color.

34. The light emitting toothbrush of claim 20, wherein at least a portion of the toothbrush body is translucent.

35. The light emitting toothbrush of claim 20, further comprising a load cell capable of measuring the force applied to the brush head portion, and configured to provide a brush force input signal to the electrical circuitry for controlling the light sources to provide feedback to an operator.

36. The light emitting toothbrush of claim 20, wherein the electrical circuitry can be configured to count the number of times the second switch is actuated.

37. The light emitting toothbrush of claim 20, wherein the electrical circuitry includes a timing device to measure the time the second switch is actuated.

* * * * *